United States Patent [19]

Tinney et al.

[11] 4,043,993

[45] Aug. 23, 1977

[54] NEW PENTAPEPTIDES AND METHODS FOR THEIR PRODUCTION

[75] Inventors: Francis John Tinney; Ernest D. Nicolaides; Alfred Campbell, all of Ann Arbor, Mich.

[73] Assignee: Parke, Davis & Company, Detroit, Mich.

[21] Appl. No.: 699,124

[22] Filed: June 23, 1976

[51] Int. Cl.² ............................................. C07C 103/52
[52] U.S. Cl. .................... 260/112.5 LH; 260/112.5 R; 424/177
[58] Field of Search ............... 260/112.5 LH, 112.5 R

[56] References Cited

U.S. PATENT DOCUMENTS 3,796,697  3/1974  Flouret .................... 260/112.5 LH

OTHER PUBLICATIONS

Biochem. and Biophys. Res. Comm. (1974) 57, 1248–1256.
Biochem. and Biophys. Res. Comm. (1974) 60, 406–412.

*Primary Examiner*—Delbert R. Phillips
*Attorney, Agent, or Firm*—Stephen Raines; David B. Ehrlinger; George M. Richards

[57] ABSTRACT

New pentapeptides having the formula X-R-Tyr-(benzyl)-Ser(benzyl)-R$^1$-Y wherein X is t-butoxycarbonyl or benzyloxycarbonyl, R is a single amino acid fragment, a dipeptide fragment or tripeptide fragment utilizing amino acids selected from the group consisting of Pro, Aze, His-(benzyl) and Trp; R$^1$ is a single bond or a single amino acid fragment or a dipeptide fragment utilizing amino acids selected from the group consisting of Ala, Trp and His and Y is lower alkoxy, hydrazino, amino, lower alkylamino or di(lower alkyl)amino with the proviso that the total number of amino acid units when R and R$^1$ are combined is three.

8 Claims, No Drawings

NEW PENTAPEPTIDES AND METHODS FOR THEIR PRODUCTION

SUMMARY AND DETAILED DESCRIPTION

The present invention relates to new peptide compounds that are useful in luteinizing hormone releasing factor antagonists and to methods for their production. More particularly, the invention relates to new N-protected pentapeptides that are represented by the formula X—R—Tyr(benzyl)-Ser(benzyl)—R$^1$—Y         I wherein X is t-butoxycarbonyl or benzyloxycarbonyl, R is a single amino acid fragment, a dipeptide fragment or tripeptide fragment utilizing amino acids selected from the group consisting of Pro, Aze, His(benzyl) and Trp; R$^1$ is a single bond or a single amino acid fragment or a dipeptide fragment utilizing amino acids selected from the group consisting of Ala, Trp and His and Y is lower alkoxy, hydrazino, amino, lower alkylamino or di(lower alkyl)amino with the proviso that the total number of amino acid units when R and R$^1$ are combined is three.

The preferred compounds of formula I are those wherein X is as previously described, R is Pro-His(benzyl), His(benzyl)-Trp, Pro-Trp or Aze-His(benzyl), R$^1$ is Ala and Y is methoxy or ethylamino.

In formula I, the conventional symbols for amino acid residues of peptide compounds linked thereto are used and each is intended to have the following meaning: Pro, D-prolyl or L-prolyl; Aze, D-2-azetidinylcarbonyl or L-2-azetidinylcarbonyl; His(benzyl), N$^{im}$-benzyl-D-histidyl or N$^{im}$-benzyl-L-histidyl; Trp, D-tryptophyl or L-tryptophyl; Ala, D-alanyl or L-alanyl; His, D-histidyl or L-histidyl; Tyr(benzyl), D-tyrosyl(benzyl) or L-tyrosyl(benzyl) and Ser(benzyl), D-seryl(benzyl) or L-seryl(benzyl). In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein X, R and R$^1$ are as previously defined and Y is lower alkoxy, are produced by removing a protected pentapeptide from a resin complex of the following structure X—R—Tyr(benzyl)-Ser(benzyl)—R$^1$-resin         II wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected pentapeptide through a methyleneoxy bridge wherein the methylene group is attached to the polymeric portion of the resin and the oxygen atom is attached to the protected pentapeptide and X, R and R$_1$ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol, for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein Y is hydrazino, amino, lower alkylamino or di(lower alkyl)amino may be prepared by reacting compounds of the formula II wherein X, R and R$^1$ are as previously defined, with hydrazine, ammonia, lower alkylamine or di(lower alkyl)amine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

The complex resins of the formula II are prepared by coupling a protected amino acid of the formula

X—R—OH         III wherein X is as previously defined and R is Pro, Aze, His(benzyl) or Trp with complex resins of the formula R$^2$—Tyr(benzyl)-Ser(benzyl)-R$^1$-resin         IV wherein R$^1$ is as previously described and R$^2$ is hydrogen, a single amino acid fragment or a dipeptide fragment utilizing the amino acids Pro, Aze, His(benzyl) or Trp with the proviso that the total number of amino acid units when R$^1$ and R$^2$ are combined is two, in an organic solvent, such as dichloromethane with the aid of dicyclohexylcarbodiimide. The three reactants may be used in about equimolar quantities, but excess amounts of the protected amino acid and dicyclohexylcabodiimide are sometimes advantageous. The reaction is generally conducted at about room temperature for a period of from about fifteen minutes to about 20 hours.

The complex resins of the formula IV are prepared by treating complex resins of the formula t-butoxycarbonyl-R$^2$-Tyr(benzyl)-Ser(benzyl)-R$^1$-resin         V wherein R$^1$ is as described in formula IV and R$^2$ is a single bond, a single amino acid fragment or a dipeptide fragment utilizing the amino acids Pro, Aze, His(benzyl) or Trp, with the proviso that the total number of amino acid units when R$^1$ and R$^2$ are combined is two with a large excess of trifluoroacetic acid utilizing dichloromethane as the solvent at temperatures of from 20° C. to 30° C. for about 10 minutes followed by neutralization of the trifluoroacetic acid salt with a base such as triethylamine.

Certain of the complex resins of formula V are prepared by coupling t-butoxycarbonyl-R$^3$—OH wherein R$^3$ is Pro, Aze, His(benzyl) or Trp, to complex resins of the formula R⁴-Tyr(benzyl)-Ser(benzyl)-R¹-resin      VI wherein R¹ is a single bond, Ala, Trp or His, R⁴ is hydrogen, Pro, Aze, His(benzyl) or Trp with the proviso that when R¹ is an amino acid R⁴ is hydrogen and when R⁴ is an amino acid, R¹ is a single bond using the reaction procedure described for the preparation of compounds of the formula II.

The complex resins of the formula VI are prepared by treating the complex resins of the formula t-butoxycarbonyl-R⁴-Tyr(benzyl)-Ser(benzyl)-R¹-resin      VII wherein R¹ is as described for formula VI and R⁴ is a single bond, Pro, Aze, His(benzyl) or Trp, with trifluoroacetic acid using the reaction procedure for the preparation of compounds of the formula IV.

Certain of the complex resins of the formula VII are prepared by coupling t-butoxycarbonyl-R⁴-OH wherein R⁴ is Pro, Aze, His(benzyl) or Trp to complex resins of the formula Tyr(benzyl)-Ser(benzyl)-R¹-resin      VIII wherein R¹ is a single bond according to the procedure used for the preparation of compounds of formula II.

The complex resins of the formula VIII are prepared by treating the complex resins of the formula t-butoxycarbonyl-Tyr(benzyl)-Ser(benzyl)-R¹-resin      IX wherein R¹ is as described in formula VIII with trifluoroacetic acid using the reaction procedure for the preparation of compounds of the formula IV.

The complex resins of the formula IX and other useful complex resins are prepared by coupling t-butoxycarbonyl-Tyr(benzyl)-OH to complex resins of the formula Ser(benzyl)-R¹-resin      X wherein R¹ is as described in formula I, according to the procedure used for the preparation of compounds of formula II.

The complex resins of the formula X are prepared by treating the complex resins of the formula t-butoxycarbonyl-Ser(benzyl)-R¹-resin      XI wherein R¹ is as described in formula I with trifluoroacetic acid using the reaction procedure for the preparation of compounds of the formula IV.

The complex resins of formula XI are prepared by coupling t-butoxycarbonyl-Ser(benzyl)-OH to complex resins of the formula R⁵-resin      XII wherein R⁵ is an amino acid or dipeptide utilizing amino acids selected from the group consisting of Ala, Trp and His, according to the procedure used for the preparation of compounds of formula II.

The complex resins of the formula XII are prepared by treating the complex resins of the formula t-butoxycarbonyl-R⁵-resin      XIII wherein R⁵ is as described in formula XII, with trifluoroacetic acid using the reaction procedure for the preparation of compounds of formula IV.

Certain of the complex resins of the formula XIII are prepared by coupling t-butoxycarbonyl-R⁶-OH      XIV wherein R⁶ is Ala, Trp or His to complex resins of the formula R⁷-resin      XV wherein R⁷ is Ala, Trp or His, according to the procedure used for the preparation of compounds of formula II.

The complex resins of the formula XV are prepared by treating the complex resins of the formula t-butoxycarbonyl-R⁷-resin      XVI wherein R⁷ is as described for formula XV, with trifluoroacetic acid using the reaction procedure for the preparation of compounds of formula IV.

In accordance with this invention, compounds of the formula I, wherein X, R and R¹ are as previously described and Y is hydrazino, amino, lower alkylamino or di(lower alkyl)amino are prepared by reacting a compound of the formula I wherein Y is alkoxy, preferably methoxy, with hydrazine, ammonia, lower alkylamine or di(lower alkylamine).

The reactions are conducted at temperatures of from about 5° C. to 100° C. for from three hours to four days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein X, R and R¹ are as previously defined and Y is amino, lower alkylamino or di(lower alkyl)amino are prepared by reacting a compound of the formula X-R-Tyr(benzyl)-Ser(benzyl)-R¹-N₃      XVII with ammonia, lower alkylamine or di(lower alkyl)amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When X is t-butoxycarbonyl, care should be taken to avoid the presence of a large excess of acid.

The azide compounds of the formula XVII are normally prepared in situ by reacting a peptide hydrazide of the formula X-R-Tyr(benzyl)-Ser(benzyl)-R¹-NHNH₂      XVIII wherein X, R and R¹ are as defined in formula I with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° C. and 0° C. following the in situ formation of the azide of formula XVII and prior to the further reaction of the peptide azide with the appropriate amine to form certain pentapeptides of formula I, a tertiary amine such as triethylamine is added to the reaction mixture to neutralize the acid used.

The compounds of formula XVIII are prepared by reacting a compound of formula I wherein Y is methoxy with hydrazine hydrate in methanol.

Compounds of the formula I wherein X, R and R¹ are as described in formula I and Y is hydrazino, amino, lower alkylamino or di(lower alkyl)amino are prepared by coupling a compound of the formula

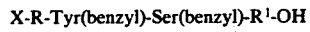

X-R-Tyr(benzyl)-Ser(benzyl)-R¹-OH       XIX with hydrazine, ammonia, a lower alkylamine or a di(-lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° C. to 50° C., preferably room temperature for periods of from ten hours to five days.

1-Hydroxybenzotriazole may also be used in the above reaction in addition to the dicyclohexylcarbodiimide. The 1-hydroxybenzotriazole is added in a ratio of one or two equivalents when compared to the reactants.

The compounds of the formula XIX are prepared by the hydrolysis of a compound of formula I wherein X, R and R¹ are as previously defined and Y is lower alkoxy. The reaction is conducted at temperatures of from 20° C. to 30° C. using about 0.5 ml. of two normal aqueous sodium hydroxide solution and 10 ml. of solvent, usually water or an alcohol such as methanol, for each millimole of ester. The compound of formula XIX is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Pentapeptides of this invention were screened for LRF antagonist activity in vitro using rat anterior pituitary cell cultures as described by Vale et. al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| N$^\alpha$-t-butoxycarbonyl-L-prolyl-N$^{im}$-benzyl-L-histidyl-O-benzyl-L-tyrosyl-O-benzyl-L-seryl-D-alanine methyl ester | $6 \times 10^{-7}$ | 14.32 | 76 |
| | $3 \times 10^{-7}$ | 16.06 | 70 |
| | $1 \times 10^{-7}$ | 20.07 | 54 |
| | $6 \times 10^{-8}$ | 21.50 | 48 |
| | $3 \times 10^{-8}$ | 22.51 | 44 |
| LRF Control | $3.5 \times 10^{-10}$ | 33.78 | |
| Saline Control | | 8.33 | |
| | $6 \times 10^{-7}$ | 9.21 | 112 |
| | $3.5 \times 10^{-7}$ | 13.10 | 98 |
| | $2 \times 10^{-7}$ | 13.57 | 97 |
| | $1 \times 10^{-7}$ | 23.02 | 64 |
| | $6 \times 10^{-8}$ | 29.34 | 42 |
| LRF Control | $3.5 \times 10^{-10}$ | 41.70 | |
| Saline Control | | 12.55 | |
| N$^\alpha$-benzyloxycarbonyl-D-2-azetidinylcarbonyl-N$^{im}$-benzyl-L-histidyl-O-benzyl-L-tyrosyl-O-benzyl-L-seryl-D-alanine methyl ester | $1 \times 10^{-6}$ | 5.72 | 102 |
| LRF Control | $2.5 \times 10^{-10}$ | 38.98 | |
| Saline Control | | 6.25 | |
| | $6 \times 10^{-7}$ | 17.18 | 89 |
| | $2.5 \times 10^{-7}$ | 22.34 | 78 |
| | $1 \times 10^{-7}$ | 33.60 | 53 |
| | $6 \times 10^{-8}$ | 44.92 | 29 |
| LRF Control | $3.5 \times 10^{-10}$ | 58.17 | |
| Saline Control | | 12.24 | |
| N$^\alpha$-butoxycarbonyl-N$^{im}$-benzyl-L-histidyl-L-tryptophyl-O-benzyl-D-tyrosyl-O-benzyl-L-seryl-D-alanine N-ethylamide | $1 \times 10^{-6}$ | 13.21 | 84 |
| LRF Control | $3.5 \times 10^{-10}$ | 42.57 | |
| Saline Control | | 7.46 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the pentapeptides of this invention are useful in controlling ovulation and in restricting fertility.

The invention is illustrated by the following examples.

EXAMPLE 1:

N$^\alpha$-t-Butoxycarbonyl-L-prolyl-N$^{im}$-benzyl-L-histidyl-O-benzyl-L-tyrosyl-O-benzyl-L-seryl-D-alanine methyl ester N$^\alpha$-t-Butoxycarbonyl-L-prolyl-N$^{im}$-benzyl-L-histidyl-O-benzyl-L-tyrosyl-O-benzyl-L-seryl-D-alanine resin, 7.4 g., is stirred with 25 ml. of triethylamine in 250 ml. of methanol for two days at room temperature. After removing the resin by filtration, the solvent is evaporated and the residue chromatographed on silica gel with chloroform-methanol-water (60:30:5) yielding the above named product; 2.4 g.; m.p. 130°–134° C.

General Procedure for the Solid Phase Synthesis of Peptide Resins

The peptide resin is obtained by attaching an α-amino protected amino acid to a resin (usually a chloromethylated resin which is commercially available from Lab Systems, Inc., San Mateo, California). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart "Solid Phase Peptide Synthesis," W. H. Freeman and Co., 1969.

Each cycle of the procedure follows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to thirty minutes agitation with the α-amino-protected amino acid in 20% molar excess (based on the resin nitrogen analysis). In an alternate method, a 4-fold excess of the α-amino-protected amino acid is agitated with the resin for fifteen minutes and the excess recovered by draining the solution from the reactor.
6. Addition of dicyclohexylcarbodiimide at least equivalent to the α-amino-protected amino acid in Step 5 in dichloromethane followed by agitation for four to twenty hours. In the alternate method, a 3.3-fold excess of dicyclohexylcarbodiimide is used relative to the α-amino-protected amino acid resin.
7. Three washes with dichloromethane.

$N^\alpha$-t-Butoxycarbonyl-L-prolyl-$N^{im}$-benzyl-L-histidyl-O-benzyl-L-tyrosyl-O-benzyl-L-seryl-D-alanine resin is obtained from 20 g. (0.0132 mol) of $N^\alpha$-t-butoxycarbonyl-D-alanine resin by successive treatment according to the above procedure using 1) 5.9 g. (0.02 mol) of $N^\alpha$-t-butoxycarbonyl-O-benzyl-L-serine and 4.1 g. (0.02 mol) of dicyclohexylcarbodiimide, 2) 7.4 g. (0.02 mol) of $N^\alpha$-t-butoxycarbonyl-O-benzyl-L-tyrosine and 4.1 g. of dicyclohexylcarbodiimide, 3) 6.9 g. (0.02 mol) of $N^\alpha$-t-butoxycarbonyl-$N^{im}$-benzyl-L-histidine and 4.1 g. of dicyclohexylcarbodiimide, and 4) with 7.2 g. of resin from 27.2 g. obtained in Step 3, 1.6 g. (0.007 mol) of $N^\alpha$-t-butoxycarbonyl-L-proline and 1.4 g. (0.007 mol) of dicyclohexylcarbodiimide.

$N^\alpha$-t-Butoxycarbonyl-D-alanine resin is obtained by mixing 100 g. of chloromethylated resin crosslinked with 1% divinylbenzene, 35 g. of $N^\alpha$-t-butoxycarbonyl-D-alanine and 18.5 g. of triethylamine in 500 ml. of ethanol at reflux for three days, filtered and washed with ethanol and ether. After drying, analysis shows 0.00066 mol of $N^\alpha$-t-butoxycarbonyl-D-alanine/gram,

EXAMPLE 2

$N^\alpha$-t-Butoxycarbonyl-L-prolyl-$N^{im}$-benzyl-L-histidyl-O-benzyl-L-tyrosyl-O-benzyl-L-seryl-D-alanine N-ethylamide The methyl ester of Example 1, 0.3 g., is let stand in an excess of ethylamine in methanol at room temperature for four days. The above named product is obtained by repeated evaporation and then triturating with ether; 0.15 g. as a hemihydrate; m.p. 135°–139° C.

EXAMPLE 3

$N^\alpha$-t-Butoxycarbonyl-D-prolyl-$N^{im}$-benzyl-L-histidyl-O-benzyl-L-tyrosyl-O-benzyl-L-seryl-D-alanine methyl ester $N^\alpha$-t-Butoxycarbonyl-D-prolyl-$N^{im}$-benzyl-L-histidyl-O-benzyl-L-tyrosyl-O-benzyl-L-seryl-D-alanine resin, 17 g., is treated with 20 ml. of triethylamine in 200 ml. of methanol at room temperature overnight. After removal of the volatile components, the oily product is precipitated from ether-petroleum ether and then from cooling isopropanol; 3 g. of product in the form of its monohydrate; m.p. 85°–87° C.

$N^\alpha$-t-Butoxycarbonyl-D-prolyl-$N^{im}$-benzyl-L-histidyl-O-benzyl-L-tyrosyl-O-benzyl-L-seryl-D-alanine resin is obtained according to the General Procedure of Example 1 from 12 g. (9.6 mmol) of $N^\alpha$-t-butoxycarbonyl-D-alanine resin by successive coupling with 1) 2.5 g. (8 mmol) of $N^\alpha$-t-butoxycarbonyl-O-benzyl-L-serine and 1.7 g. of dicyclohexylcarbodiimide, 2) 3.0 g. (8 mmol) of $N^\alpha$-t-butoxycarbonyl-O-benzyl-tyrosine and 1.7 g. of dicyclohexylcarbodiimide, 3) 2.8 g. (8 mmol) of $N^\alpha$-t-butoxycarbonyl-$N^{im}$-benzyl-L-histidine and 1.7 g. of dicyclohexylcarbodiimide and 4) 1.8 g. (8 mmol) of $N^\alpha$-t-butoxycarbonyl-D-proline and 1.7 g. of dicyclohexylcarbodiimide.

EXAMPLE 4

$N^\alpha$-t-Butoxycarbonyl-D-prolyl-$N^{im}$-benzyl-L-histidyl-O-benzyl-L-tyrosyl-O-benzyl-L-seryl-D-alanine N-ethylamide The methyl ester of Example 3, 700 mg., is treated with 20 ml. of methanol, 10 ml. of dimethylformamide and 10 ml. of ethylamine at room temperature for five days. The evaporation residue was precipitated from cooling isopropanol yielding 200 mg. of the above named product in the form of its monohydrate; m.p. 160°–161° C.

EXAMPLE 5

$N^\alpha$-Benzyloxycarbonyl-L-2-azetidinylcarbonyl-$N^{im}$-benzyl-L-histidyl-O-benzyl-L-tyrosyl-O-benzyl-L-seryl-D-alanine methyl ester Nα-Benzyloxycarbonyl-L-2-azetidinylcarbonyl-$N^{im}$-benzyl-L-histidyl-O-benzyl-L-tyrosyl-O-benzyl-L-seryl-D-alanine resin is treated with 150 ml. of methanol, 50 ml. of dimethylformamide and 20 ml. of triethylamine at room temperature for 16 hours. The mixture is warmed and filtered. The resin is washed with dimethylformamide and the filtrates evaporated. The residue precipitates from ether-petroleum ether as a semisolid which is re-precipitated from ether-isopropanol to yield 4.1 g., m.p. 166°–167° C.

$N^\alpha$-Benzyloxycarbonyl-L-2-azetidinylcarbonyl-$N^{im}$-benzyl-L-histidyl-O-benzyl-L-tyrosyl-O-benzyl-L-seryl-D-alanine resin is obtained according to the General Procedure of Example 1 from $N^\alpha$-t-butoxycarbonyl-D-alanine resin, 10 g., 8.8 mmol, using 1) 2.8 g., 9.2 mmol, of $N^\alpha$-t-butoxycarbonyl-O-benzyl-L-serine and 2 g., 9.7 mmol of dicyclohexylcarbodiimide, 2) 3.4 g., 9.15 mmol, of $N^\alpha$-t-butoxycarbonyl-O-benzyl-L-tyrosine and 2 g., 9.7 mmol, of dicyclohexylcarbodiimide, 3) 3 g., 8.7 mmol, of $N^\alpha$-t-butoxycarbonyl-$N^{im}$-benzyl-L-histidine and 2 g., 9.7 mmol, of dicyclohexylcarbodiimide and 4) 2.2 g., 9.35 mmol, of N$^\alpha$-benzyloxycarbonyl-L-2-azetidine carboxylic acid and 2 g., 9.7 mmol, of dicyclohexylcarbodiimide.

N$^\alpha$-Benzyloxycarbonyl-L-2-azetidine carboxylic acid is obtained from the known L-azetidine-2-carboxylic acid [Phillips and Cromwell, J. Hetero. Chem., 10, 795 (1973); Rodebaugh and Cromwell, J. Hetero. Chem. 6, 993 (1969)].

EXAMPLE 6

N$^\alpha$-Benzyloxycarbonyl-L-2-azetidinylcarbonyl-N$^{im}$-benzyl-L-histidyl-O-benzyl-L-tyrosyl-O-benzyl-L-seryl-D-alanine N-ethylamide The methyl ester of Example 5, 500 mg., is dissolved in 75 ml. of methanol and 10 ml. of ethylamine added. The reaction is kept at 25° C. for eighteen hours and then evaporated and the residue triturated with ether to yield the above named product; 450 mg; m.p. 173°–175° C.

EXAMPLE 7

N$^\alpha$-Burlorycarbonyl-N-$^{im}$-benzyl-L-histidyl-O-benzyl-L-tyrosyl-O-benzyl-L-seryl-L-histidyl-D-alanine N-ethylamide N$^\alpha$-Butoxycarbonyl-N$^{im}$-benzyl-L-histidyl-O-benzyl-L-tyrosyl-O-benzyl-L-seryl-L-histidyl-D-alanine methyl ester, 0.3 g., (Example 18) is treated with 200 ml. of methanol and 5 ml. of ethylamine at room temperature for three days. The above named product is isolated after evaporation of the solvent and the chromatographing of the residue on a silica gel column with ten percent methanol in benzene; 0.21 g.; m.p. 83°–88° C.

EXAMPLE 8

N$^\alpha$-t-Butoxycarbonyl-N$^{im}$-benzyl-L-histidyl-L-tryptophyl-O-benzyl-D-tyrosyl-O-benzyl-L-seryl-D-alanine methyl ester N$^\alpha$-t-Butoxycarbonyl-N$^{im}$-benzyl-L-histidyl-L-tryptophyl-O-benzyl-D-tyrosyl-O-benzyl-L-seryl-D-alanine resin, 7.6 g., is stirred in a solution of ten percent triethylamine in methanol for several days. The green solution, after separation of the resin, is decolorized with carbon and filtered through a Celite filter aid. Crystallization of the above named product occurs during solvent evaporation, 1.72 g. as a hemihydrate; m.p. 88°–103° C.

N$^\alpha$-t-Butoxycarbonyl-N$^{im}$-benzyl-L-histidyl-L-tryptophyl-O-benzyl-D-tyrosyl-O-benzyl-L-seryl-D-alanine resin is obtained from 40 g. (32 mmol) of N$^\alpha$-t-butoxycarbonyl-D-alanine resin according to the General Procedure of Example 1 by successive couplings with 1) 10.7 g. (35 mmol) of N$^\alpha$-t-butoxycarbonyl-O-benzyl-L-serine and 7.21 g. (35 mmol) of dicyclohexylcarbodiimide, 2) using 20 g. of the 58 g. of resin obtained in Step 1, with 7.0 g. (19 mmol) of N$^\alpha$-t-butoxycarbonyl-O-benzyl-D-tyrosine and 3.9 g. (19 mmol) of dicyclohexylcarbodiimide, 3) using 14 g. of the 21 g. of resin obtained in Step 2, with 4.0 g. (13 mmol) of N$^\alpha$-t-butoxycarbonyl-L-tryptophan and 2.7 g. (13 mmol) of dicyclohexylcarbodiimide and 4) using 7.5 g. (3.7 mmol) of the 14.9 g. of resin obtained in Step 3, with 2.4 g. (7 mmol) of N$^\alpha$-t-butoxycarbonyl-N$^{im}$-benzyl-L-histidine and 1.44 g. (7 mmol) of dicyclohexylcarbodiimide.

N$^\alpha$-Butoxycarbonyl-O-benzyl-D-tyrosine is obtained by stirring a solution of equivalent amounts of O-benzyl-D-tyrosine, t-butoxycarbonylazide and powered magnesium oxide in 50% dioxane in water for one week. The mixture is warmed and filtered and the filtrate evaporated to a yellow oil. The oil is suspended in water and neutralized with citric acid. The mixture is extrated with ethyl acetate and the organic solution washed with saturated sodium chloride solution and dried. Evaporation of the solvent yields an oil which is crystallized by trituration with petroleum ether; 24% yield.

EXAMPLE 9

N$^\alpha$-Butoxycarbonyl-N$^{im}$-benzyl-L-histidyl-L-tryptophyl-O-benzyl-D-tyrosyl-O-benzyl-L-seryl-D-alanine N-ethylamide The methyl ester of Example 8, 600 mg., is treated with 30 ml. of methanol and 10 ml. of ethylamine in a closed container for several days. After evaporation of the volatile components, the residue is crystallized from petroleum ether giving the above named product; 550 mg., m.p. 105°–128° C.

EXAMPLE 10

N$^\alpha$-t-Butoxycarbonyl-D-prolyl-L-tryptophyl-O-benzyl-L-tyrosyl-O-benzyl-L-seryl-D-alanine methyl ester Ethanol and then ether washed N$^\alpha$-t-butoxycarbonyl-D-prolyl-L-tryptophyl-O-benzyl-L-tyrosyl-O-benzyl-L-seryl-D-alanine resin, 15.5 g., is stirred overnight in a solution containing 10 percent by volume triethylamine in methanol. After filtration and evaporation, the crude above named product is a glass which is precipitated from cooling isopropanol; 4.5; m.p. 105°–110° C.

N$^\alpha$-t-Butoxycarbonyl-D-prolyl-L-tryptophyl-O-benzyl-L-tyrosyl-O-benzyl-L-seryl-D-alanine resin is obtained according to the General Procedure of Example 1 from 10 g., 8.8 mmol, of N$^\alpha$-t-butoxycarbonyl-D-alanine resin by successive couplings with 1) 2.8 g. (9.15 mmol) of N$^\alpha$-t-butoxycarbonyl-O-benzyl-L-serine and 1.9 g. (9.2 mmol) of dicyclohexylcarbodiimide, 2) 3.4 g. (9.15 mmol) of N$^\alpha$-t-butoxycarbonyl-O-benzyl-L-tyrosine and 1.9 g. of dicyclohexylcarbodiimide, 3) 2.8 g. (9.15 mmol) of N$^\alpha$-t-butoxycarbonyl-L-tryptophan and 1.9 g. of dicyclohexylcarbodiimide and 4) 1.9 g. (8.8 mmol) of N$^\alpha$-t-butoxycarbonyl-D-proline and 1.9 g. of dicyclohexylcarbodiimide.

N$^\alpha$-t-Butoxycarbonyl-D-proline is obtained by reacting D-proline with t-butoxycarbonylazide in the presence of magnesium oxide in the manner described in Example 8 for the preparation of N$^\alpha$-t-butoxycarbonyl-O-benzyl-D-tyrosine; m.p. 126°–127° C.

EXAMPLE 11

N$^\alpha$-t-Butoxycarbonyl-D-prolyl-L-tryptophyl-O-benzyl-L-tyrosyl-O-benzyl-L-seryl-D-alanine N-ethylamide The methyl ester of Example 10, 1 g., is treated with 10 ml. of ethylamine and 20 ml. of methanol followed by evaporation of volatile materials. Trituration of the above named product with ether gives 800 mg. of white solid; m.p. 228°–229° C.

EXAMPLE 12

N$^\alpha$-t-Butoxycarbonyl-N$^{im}$-benzyl-L-histidyl-O-benzyl-L-tyrosyl-O-benzyl-L-seryl-L-tryptophyl-D-alanine methyl ester N$^\alpha$-t-Butoxycarbonyl-N$^{im}$-benzyl-L-histidyl-O-benzyl-L-tyrosyl-O-benzyl-L-seryl-L-tryptophyl-D-alanine resin, 6 g., is treated with 30 ml. of triethylamine in 300 ml. of methanol at room temperature for two days.

After filtration, the solution is evaporated and the residue chromatographed on silica gel with chloroform-methanol-water (60:30:5) to give the above named product; 1.4 g.; m.p. 102°-107° C.

$N^\alpha$-t-Butoxycarbonyl-$N^{im}$-benzyl-L-histidyl-O-benzyl-L-tyrosyl-O-benzyl-L-seryl-L-tryptophyl-D-alanine resin is obtained from 50 g. (0.0315 mol) of $N^\alpha$-t-butoxycarbonyl-D-alanine resin according to the General Procedure of Example 1 by successive couplings with 1) 14.4 g. (0.0473 mol) of $N^\alpha$-t-butoxycarbonyl-L-tryptophan and 9.7 g. (0.0473 mol) of dicyclohexylcarbodiimide, 2) 14.0 g. (0.0473 mol) of $N^\alpha$-t-butoxycarbonyl-O-benzyl-L-serine and 9.7 g. of dicyclohexylcarbodiimide, 3) 17.5 g. (0.0473 mol) of $N^\alpha$-t-butoxycarbonyl-O-benzyl-L-tyrosine and 9.7 g. dicyclohexylcarbodiimide and 4) using 61 g. of resin wet cake from 342 g. obtained in Step 3, 2.9 g. (0.0084 mol) of $N^\alpha$-t-butoxycarbonyl-$N^{im}$-benzyl-L-histidine and 1.73 g. (0.0084 mol) of dicyclohexylcarbodiimide.

EXAMPLE 13

$N^\alpha$-t-Butoxycarbonyl-$N^{im}$-benzyl-L-histidyl-O-benzyl-L-tyrosyl-O-benzyl-L-seryl-L-tryptophyl-D-alanine N-ethylamide The methyl ester of Example 12, 0.3 g., is treated with 5 ml. of ethylamine in 200 ml. of methanol at room temperature for four days. The above named product is isolated by repeated evaporation of methanol solvent, followed by trituration with ether; 0.2 g. as a hemihydrate; m.p. 111°-116° C.

EXAMPLE 14

$N^\alpha$-t-Butoxycarbonyl-$N^{im}$-benzyl-L-histidyl-O-benzyl-L-tyrosyl-O-benzyl-L-seryl-L-tryptophyl-D-alaninamide The methyl ester of Example 12, 0.3 g., is reacted with 100 ml. of methanolic ammonia for two days at room temperature. The crude evaporation residue is chromatographed on silica gel with chloroform-methanol-water (60:30:5) giving the product in the form of its sesquihydrate, 0.25 g.; m.p. 115°-120° C.

EXAMPLE 15

$N^\alpha$-t-Butoxycarbonyl-$N^{im}$-benzyl-L-histidyl-O-benzyl-L-tyrosyl-O-benzyl-L-seryl-L-tryptophyl-D-alanyl hydrazide The methyl ester of Example 12, 0.3 g., is reacted with 150 ml. of methanol and 1 g. of hydrazine hydrate at room temperature for two days. The crude above named product is chromatographed on silica gel with chloroform-methanol-water (60:30:5); 0.23 g. as a monohydrate; m.p. 152°-157° C.

EXAMPLE 16

$N^\alpha$-t-Butoxycarbonyl-$N^{im}$-benzyl-L-histidyl-O-benzyl-L-tyrosyl-O-benzyl-L-seryl-L-tryptophyl-D-alanine N-methylamide The methyl ester of Example 12, 0.2 g., is reacted with 100 ml. of methanol and 5 g. of 40% methylamine in water at room temperature for two days. The mixture is evaporated and the residue taken into methanol and the solvent evaporated. The resultant above named product is triturated with ether; 0.11 g. as a monohydrate; m.p. 115°-120° C.

EXAMPLE 17

$N^\alpha$-t-Butoxycarbonyl-L-prolyl-$N^{im}$-benzyl-L-histidyl-O-benzyl-L-tyrosyl-O-benzyl-L-seryl-D-alaninamide The methyl ester of Example 1, 0.3 g., is treated with an excess of methanol saturated with ammonia at room temperature for four days. The above named product is obtained by repeated evaporation and then triturating with ether; 0.23 g. as a hemihydrate; m.p. 158°-163° C.

EXAMPLE 18

$N^\alpha$-t-Butoxycarbonyl-$N^{im}$-benzyl-L-histidyl-O-benzyl-L-tyrosyl-O-benzyl-L-seryl-L-histidyl-D-alanine methyl ester $N^\alpha$-t-Butoxycarbonyl-$N^{im}$-benzyl-L-histidyl-O-benzyl-L-tyrosyl-O-benzyl-L-seryl-$N^{im}$-tosyl-L-histidyl-D-alanine resin, 5.8 g., is treated with methanol, 500 ml., and triethylamine, 50 ml., at room temperature for two days, filtered and the filtrate evaporated. The crude product is chromatographed on silica gel with benzene-methanol (90:10) giving 1.6 g. of the above named product in the form of its hydrate; m.p. 140°-145° C.

The $N^\alpha$-t-butoxycarbonyl-$N^{im}$-benzyl-L-histidyl-O-benzyl-L-tyrosyl-O-benzyl-L-seryl-$N^{im}$-tosyl-L-histidyl-D-alanine resin is obtained by the General Procedure of Example 1 using 10 g. (0.0066 mol) of $N^\alpha$-t-butoxycarbonyl-D-alanine resin with 1) 4.2 g. (0.01 mol) of $N^\alpha$-t-butoxycarbonyl-$N^{im}$-tosyl-L-histidine and 2.1 g. (0.01 mol) of dicyclohexylcarbodiimide, 2) 3.0 g. (0.01 mol) of $N^\alpha$-t-butoxycarbonyl-O-benzyl-L-serine and 2.1 g. (0.01 mol) of dicyclohexylcarbodiimide, 3) 3.7 g. (0.01 mol) of $N^\alpha$-t-butoxycarbonyl-O-benzyl-L-tyrosine and 2.1 g. (0.01 mol) or dicyclohexylcarbodiimide and finally 4) with 5.6 g. of resin from 11.6 g. obtained in Step 3, 2.0 g. (0.0058 mol) of $N^\alpha$-t-butoxycarbonyl-$N^{im}$-benzyl-L-histidine and 1.1 g. (0.0053 mol) of dicyclohexylcarbodiimide.

EXAMPLE 19

$N^\alpha$-t-Butoxycarbonyl-L-prolyl-O-benzyl-L-tyrosyl-O-benzyl-L-seryl-L-tryptophyl-D-alanine methyl ester $N^\alpha$-t-Butoxycarbonyl-L-prolyl-O-benzyl-L-tyrosyl-O-benzyl-L-seryl-L-tryptophyl-D-alanine resin, 6.7 g., is treated with methanol, 800 ml., and triethylamine, 80 ml., at room temperature for two days, filtered and the filtrate evaporated. The crude product is chromatographed on silica gel with chloroform-methanol-water (60:30:5) to give 2.1 g. Recrystallization from isopropanol-ether gave the pure above named product 1.2 g.; m.p. 158°-162° C.

The $N^\alpha$-t-butoxycarbonyl-L-prolyl-O-benzyl-L-tyrosyl-O-benzyl-L-seryl-L-tryptophyl-D-alanine resin is obtained by the General Procedure of Example 1 using 30 g. (0.0198 mol) of $N^\alpha$-t-butoxycarbonyl-D-alanine resin with 1) 9.1 g. (0.03 mol) of $N^\alpha$-t-butoxycarbonyl-L-tryptophane and 6.8 g. (0.033 mol) of dicyclohexylcarbodiimide, 2) 8.9 g. (0.03 mol) of $N^\alpha$-t-butoxycarbonyl-O-benzyl-L-serine and 6.8 g. (0.033 mol) of dicyclohexylcarbodiimide, 3) 11.1 g. (0.03 mol) of $N^\alpha$-t-butoxycarbonyl-O-benzyl-L-tyrosine and 6.8 g. (0.033 mol) of dicyclohexylcarbodiimide and finally 4) with 5.5 g. of resin from 41.8 g. obtained in Step 3, 2.0 g. (0.009 mol) of $N^\alpha$-t-butoxycarbonyl-L-proline and 3.0 g. (0.0146 mol) of dicyclohexylcarbodiimide.

EXAMPLE 20

$N^\alpha$-t-Butoxycarbonyl-L-prolyl-O-benzyl-L-tyrosyl-O-benzyl-L-seryl-L-tryptophyl-D-alaninamide The methyl ester of Example 19, 0.3 g., is reacted with 100 ml. of methanol saturated with ammonia at room temperature for two days. After removal of the methanol and ammonia by evaporation, the crude product is chromatographed on silica gel using chloroform-methanol-water (60:30:5) to give 0.21 g. of the above named product; m.p. 200°–205° C.

EXAMPLE 21

$N^\alpha$-t-Butoxycarbonyl-L-prolyl-O-benzyl-L-tyrosyl-O-benzyl-L-seryl-L-tryptophyl-D-alanine N-ethylamide The methyl ester from Example 19, 0.3 g., is reacted with 5 g. of ethylamine and 100 ml. of methanol at room temperature for four days. The above named product, 0.2 g., is obtained as a hemihydrate after evaporation and trituration with ether; m.p. 180°–185° C.

EXAMPLE 22

$N^\alpha$-t-Butoxycarbonyl-$N^{im}$-benzyl-D-histidyl-L-tryptophyl-O-benzyl-L-tyrosyl-O-benzyl-L-seryl-D-alanine methyl ester The washed resin, $N^\alpha$-t-butoxycarbonyl-$N^{im}$-benzyl-D-histidyl-L-tryptophyl-O-benzyl-L-tyrosyl-O-benzyl-L-seryl-D-alanine resin is stirred overnight with 200 ml. of methanol, 50 ml. of dimethylformamide and 20 ml. of triethylamine. Evaporation of solvent and trituration of the residue gives the above named product, a tan solid, which is precipitated from cooled isopropanol, dissolved in methanol, filtered and precipitated with ether; 600 mg.; m.p. 196°–197° C.

$N^\alpha$-t-Butoxycarbonyl-$N^{im}$-benzyl-D-histidyl-L-tryptophyl-O-benzyl-L-tyrosyl-O-benzyl-L-seryl-D-alanine resin is obtained according to the General Procedure of Example 1 from 12 g. (9.6 mmol) of $N^\alpha$-t-butoxycarbonyl-D-alanine resin by successive couplings with 1) 2.5 g. (8 mmol) of $N^\alpha$-t-butoxycarbonyl-O-benzyl-L-serine and 1.7 g. (8.3 mmol) of dicyclohexylcarbodiimide, 2) 3 g. (8 mmol) of $N^\alpha$-t-butoxycarbonyl-O-benzyl-L-tyrosine and 1.7 g. of dicyclohexylcarbodiimide, 3) 2.5 g. of $N^\alpha$-t-butoxycarbonyl-L-tryptophan and 1.7 g. of dicyclohexylcarbodiimide and 4) 3 g. (8 mmol) of $N^\alpha$-t-butoxycarbonyl-$N^{im}$-benzyl-D-histidine and 1.8 g. of dicyclohexylcarbodiimide.

EXAMPLE 23

$N^\alpha$-t-Butoxycarbonyl-$N^{im}$-benzyl-D-histidyl-L-tryptophyl-O-benzyl-L-tyrosyl-O-benzyl-L-seryl-D-alanine N-ethylamide The methyl ester of Example 22, 300 mg., is treated with 30 ml. of methanol and 10 ml. of ethylamine at 25° C. for two days. Trituration of the residue after evaporation with ether gives the above named product; 350 mg.; m.p. 185°–186° C.

EXAMPLE 24

$N^\alpha$-t-Butoxycarbonyl-L-tryptophyl-L-prolyl-L-prolyl-O-benzyl-L-tyrosyl-O-benzyl-L-serine methyl ester $N^\alpha$-t-Butoxycarbonyl-L-tryptophyl-L-prolyl-L-prolyl-O-benzyl-L-tyrosyl-O-benzyl-L-serine resin, 20 g., (24 mmol) is converted to the methyl ester by the procedure of Example 1 yielding the above named product in the form of a glass $[\alpha]_D^{23}$ −68° (c. 1.05 in methanol).

The above resin is prepared according to the procedure of Example 1 using $N^\alpha$-t-butoxycarbonyl-O-benzyl-L-serine resin which is successively reacted with 1) 8.9 g. (24 mmol) of $N^\alpha$-t-butoxycarbonyl-O-benzyl-L-tyrosine and 5 g. (24.2 mmol) of dicyclohexylcarbodiimide, 2) 5.0 g. (23.2 mmol) of $N^\alpha$-t-butoxycarbonyl-L-proline and 5.0 g, of dicyclohexylcarbodiimide, 3) 5 g. (23.2 mmol) of $N^\alpha$-t-butoxycarbonyl-L-proline and 5.0 g. of dicyclohexylcarbodiimide and 4) 7.30 g. (24 mmol) of $N^\alpha$-t-butoxycarbonyl-L-tryptophane and 5 g. (23.2 mmol) dicyclohexylcarbodiimide.

EXAMPLE 25

$N^\alpha$-t-Butoxycarbonyl-L-tryptophyl-L-prolyl-L-prolyl-O-benzyl-L-tyrosyl-O-benzyl-L-serine hydrazide $N^\alpha$-t-Butoxycarbonyl-L-tryptophyl-L-prolyl-L-prolyl-O-benzyl-L-tyrosyl-O-benzyl-L-serine methyl ester (0.5 g.) is stirred in a solution of 1 ml. of hydrazine hydrate and 10 ml. of ethanol. The solution is refluxed for one hour and let stand at room temperature over night. The precipitate is collected and purified by precipitation from methanol with ether (two times) yielding 275 mg. of product; $[\alpha]_D^{23}$ −70° (c. 1.01 in methanol).

EXAMPLE 26

$N^\alpha$-t-Butoxycarbonyl-L-tryptophyl-L-prolyl-L-prolyl-O-benzyl-L-tyrosyl-O-benzyl-L-serine-N-ethylamide $N^\alpha$-t-Butoxycarbonyl-L-tryptophyl-L-prolyl-L-prolyl-O-benzyl-L-tyrosyl-O-benzyl-L-serine methyl ester, 1.0 g., is dissolved in 50 ml. of a mixture of methyl alcohol and ethylamine (50:50). The solution is let stand at room temperature for one day. After removal of the solvent, the crude product is purified by chromatography over silica gel in ethyl acetate-methanol (90:10) solution to give 0.6 g. of the above named product as a white glass $[\alpha]_D^{23}$ −70° (c. 1.02 in methanol).

EXAMPLE 27

$N^\alpha$-t-Butoxycarbonyl-L-tryptophyl-L-prolyl-L-prolyl-O-benzyl-L-tyrosyl-O-benzyl-L-serinamide $N^\alpha$-t-Butoxycarbonyl-L-tryptophyl-L-prolyl-L-prolyl-O-benzyl-L-tyrosyl-O-benzyl-L-serine methyl ester (0.5 g.) is dissolved in methanol, 25 ml., and the solution saturated with gaseous ammonia. The reaction is let stand for three days at room temperature, and the solvent then removed by evaporation.

The crude product is purified by chromatography over silica geel in ethyl acetate-methanol (80:20) to give 0.2 g. of the above named product as a white glass $[\alpha]_D^{23}$ −69° (c. 1.05 in methanol).

EXAMPLE 28

N-Benzyloxycarbonyl-D-2-azetidinecarbonyl-$N^{im}$-benzyl-L-histidyl-O-benzyl-L-tyrosyl-O-benzyl-L-seryl-D-alanine methyl ester N-Benzyloxycarbonyl-D-2-azetidinecarbonyl-$N^{im}$-benzyl-L-histidyl-O-benzyl-L-tyrosyl-O-benzyl-L-seryl-D-alanine resin is treated with 150 ml. of methanol, 50 ml. of dimethylformamide and 20 ml. of triethylamine at room temperature for 16 hours. The mixture is warmed and filtered. The resin is washed with dimethylformamide and the filtrates evaporated. The residue precipitates from ether-petroleum ether as a semi-solid which is re-precipitated from ether-isopropanol to yield 4.1 g. of the above named product; m.p. 84°–85° C.

N-Benzyloxycarbonyl-D-2-azetidinecarbonyl-$N^{im}$-benzyl-L-histidyl-O-benzyl-L-tyrosyl-O-benzyl-L-seryl-D-alanine resin is obtained from $N^\alpha$-t-butoxycarbonyl-D-alanine resin, 10 g. (8.8 mmol), according to the General Procedure of Example 1 using 1) 2.8 g. (9.2 mmol) of $N^\alpha$-t-butoxycarbonyl-O-benzyl-L-serine and 2 g. (9.7 mmol) 2) 3.4 g. (9.15 mmol) of $N^\alpha$-t-butoxycarbonyl-O-benzyl-L-tyrosine and 2 g. (9.7 mmol) of dicyclohexylcarbodiimide, 3) 3 g. (8.7 mmol) of $N^\alpha$-t-butoxycarbonyl-$N^{im}$-benzyl-L-histidine and 2 g. (9.7 mmol) of dicyclohexylcarbodiimide and 4) 2.2 g. (9.35 mmol) of N-benzyloxycarbonyl-D-2-azetidinecarboxylic acid and 2 g. (9.7 mmol) of dicyclohexylcarbodiimide.

N-Benzyloxycarbonyl-D-2-azetidine carboxylic acid is obtained from the known D-azetidine-2-carboxylic acid [Phillips and Cromwell, J. Hetero. Chem., 10, 795 (1973); Rodebaugh and Cromwell, J. Hetero. Chem., 6, 993 (1969)].

We claim:

1. A pentapeptide of the formula

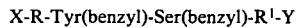

X-R-Tyr(benzyl)-Ser(benzyl)-$R^1$-Y wherein X is t-butoxycarbonyl or benzyloxycarbonyl, R is a single amino acid fragment, a dipeptide fragment or tripeptide fragment utilizing amino acids selected from the group consisting of Pro. Aze, His(benzyl) and Trp; $R^1$ is a single bond or a single amino acid fragment or a dipeptide fragment utilizing amino acids selected from the group consisting of Ala, Trp and His and Y is lower alkoxy, hydrazino, amino, lower alkylamino or di(lower alkyl)amino with the proviso that the total number of amino acid units when R and $R^1$ are combined is three.

2. The pentapeptides of claim 1 wherein R is Pro-His(benzyl), His(benzyl)-Trp, Pro-Trp or Aze-His(benzyl), $R^1$ is Ala and Y is methoxy or ethylamino.

3. The pentapeptide of claim 1 having the name $N^\alpha$-t-butoxycarbonyl-L-prolyl-$N^{im}$-benzyl-L-histidyl-L-tyrosyl-(benzyl)-L-seryl(benzyl)-D-alanine methyl ester.

4. The pentapeptide of claim 1 having the name $N^\alpha$-t-butoxycarbonyl-D-prolyl-$N^{im}$-benzyl-L-histidyl-L-tyrosyl-(benzyl)-L-seryl(benzyl)-D-alanine methyl ester.

5. The pentapeptide of claim 1 having the name $N^\alpha$-t-butoxycarbonyl-D-prolyl-$N^{im}$-benzyl-L-histidyl-L-tyrosyl-(benzyl)-L-seryl(benzyl)-D-alanine N-ethylamide.

6. The pentapeptide of claim 1 having the name $N^\alpha$-t-butoxycarbonyl-$N^{im}$-benzyl-L-histidyl-L-tryptophyl-D-tyrosyl(benzyl)-L-seryl(benzyl)-D-alanine N-ethylamide.

7. The pentapeptide of claim 1 having the name $N^\alpha$-t-butoxycarbonyl-D-prolyl-L-tryptophyl-L-tyrosyl(benzyl)-L-seryl(benzyl)-D-alanine methyl ester.

8. The pentapeptide of claim 1 having the name $N^\alpha$-benzyloxycarbonyl-L-2-azetidinylcarbonyl-$N^{im}$-benzyl-L-histidyl-L-tyrosyl(benzyl)-L-seryl(benzyl)-D-alanine methyl ester.

* * * * *